(12) United States Patent
Liu et al.

(10) Patent No.: US 10,233,263 B1
(45) Date of Patent: Mar. 19, 2019

(54) METHOD FOR PREPARATION OF SUGAMMADEX SODIUM

(71) Applicant: FORMOSA LABORATORIES, INC., Taoyuan (TW)

(72) Inventors: Yu-Liang Liu, Taoyuan (TW); Ching-Peng Wei, Taoyuan (TW)

(73) Assignee: FORMOSA LABORATORIES, INC., Taoyuan (TW)

( * ) Notice: Subject to any disclaimer, the term of this patent is extended or adjusted under 35 U.S.C. 154(b) by 0 days.

(21) Appl. No.: 15/683,795

(22) Filed: Aug. 23, 2017

(51) Int. Cl.
| | | |
|---|---|---|
| *B01D 61/02* | (2006.01) | |
| *B01D 61/40* | (2006.01) | |
| *C07B 45/06* | (2006.01) | |
| *C07B 47/00* | (2006.01) | |
| *C08B 37/00* | (2006.01) | |
| *C08B 37/16* | (2006.01) | |
| *A61K 31/724* | (2006.01) | |

(52) U.S. Cl.
CPC ........ *C08B 37/0012* (2013.01); *A61K 31/724* (2013.01); *B01D 61/02* (2013.01); *B01D 61/40* (2013.01); *C07B 45/06* (2013.01); *C07B 47/00* (2013.01); *C08B 37/0003* (2013.01)

(58) Field of Classification Search
None
See application file for complete search history.

(56) References Cited

U.S. PATENT DOCUMENTS

| | | | |
|---|---|---|---|
| 9,120,876 B2* | 9/2015 | Davuluri | C08B 37/0012 |
| 2004/0029833 A1* | 2/2004 | Zhang | A61K 31/724 |
| | | | 514/58 |

FOREIGN PATENT DOCUMENTS

WO WO-2017144734 A2 * 8/2017 ......... C08B 37/0012

OTHER PUBLICATIONS

Fletcher, Org. Chem. Front, 2015, 2, 739-752.*
Adam, J. Med. Chem. 2002, 45, 1806-1816.*

* cited by examiner

*Primary Examiner* — Layla D Berry
(74) *Attorney, Agent, or Firm* — Hannah M. Tien

(57) ABSTRACT

The present invention provides a method for improved preparation of Sugammadex sodium.

13 Claims, 10 Drawing Sheets

FIGURE 1

Synthetic scheme of Sugammadex

METHOD FOR PREPARATION OF SUGAMMADEX SODIUM

FIELD OF THE INVENTION

The present invention relates to a method for preparation of Sugammadex sodium.

BACKGROUND OF THE INVENTION

Sugammadex (Trade name: Bridion) is first disclosed in U.S. Pat. No. 6,670,340 assigned to Akzo Nobel. Sugammadex sodium was approved in EMEA as an agent for reversal of neuromuscular blockade by the agent rocuronium in general anaesthesia in 2008 and is the first selective relaxant binding agent (SRBA).

Sugammadex sodium contains 8 recurring glucose units each with 5 asymmetric carbon atoms, in total 40 asymmetric carbon atoms for the whole molecule.

Sugammadex is a modified γ-cyclodextrin, with a lipophilic core and a hydrophilic periphery. The gamma cyclodextrin has been modified from its natural state by placing eight carboxyl thio ether groups at the sixth carbon positions.

The U.S. Pat. No. 6,670,340 assigned to Akzo Nobel discloses a process for preparing Sugammadex sodium as depicted in Scheme-I:

Scheme-I cyclodextrin

-continued

The first step in the process in the scheme-I involves the preparation of Vilsmeier Hack reagent by the reaction of DMF, triphenylphosphine and Iodine. The triphenylphosphine oxide is formed as a byproduct of the first step. Removal of triphenylphosphine oxide from the product is very difficult from the reaction mass as it requires repeated washing with DMF under argon atmosphere, which leads to inconsistency in yield of final product Sugammadex.

The second step involves the reaction of 6-perdeoxy-6-per-Iodo-Gamma cyclodextrin with 3-mercapto propionic acid in presence of alkali metal hydrides in an organic solvent to give 6-per-deoxy-6-per-(2-carboxyethyl)thio-γ-cyclodextrin sodium salt.

The PCT publication WO2012/025937 discloses preparation of Sugammadex involving the reaction of gamma cyclodextrin with phosphorous halide in presence of organic solvent, thereby overcomes the formation of triphenyl phosphine oxide. The publication also discloses the use of 6-per deoxy-6-per-chloro-γ-cyclodextrin in the preparation of the Sugammadex.

The purification techniques in the prior arts are costly and not convenient in large scale operations.

There is still a need to develop simple, convenient, and efficient synthesis process for preparation of Sugammadex.

SUMMARY OF THE INVENTION

The present invention provides a method for preparation of Sugammadex sodium, comprising: (a) reacting gamma-cyclodextrin with tri-n-butylphosphine and $X_2$ in an organic solvent to obtain a compound of Formula I, wherein X is F, Cl, Br, or I;

Formula I (b) reacting the compound of Formula I with methyl 3-mercaptopropionate in presence of alkali metal hydride in an organic solvent at a temperature lower than 50° C. to obtain a compound of Formula II, and Formula II (c) reacting the compound of Formula II with sodium hydroxide to the Sugammadex sodium.

DETAILED DESCRIPTION OF THE INVENTION

Figure 1:
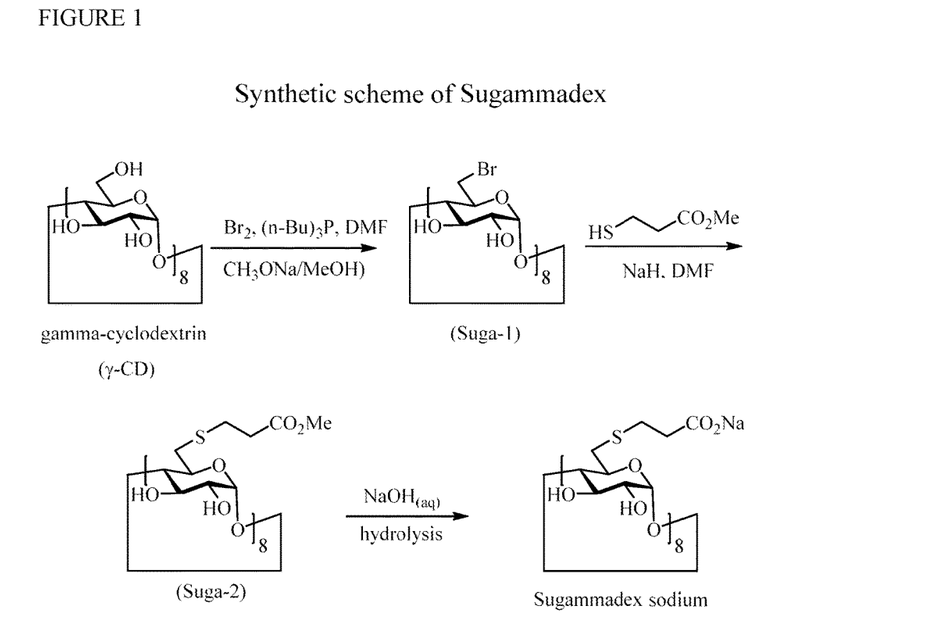
FIG. 1 illustrates one embodiment of the preparation of the Sugammadex sodium.
Figure 2:
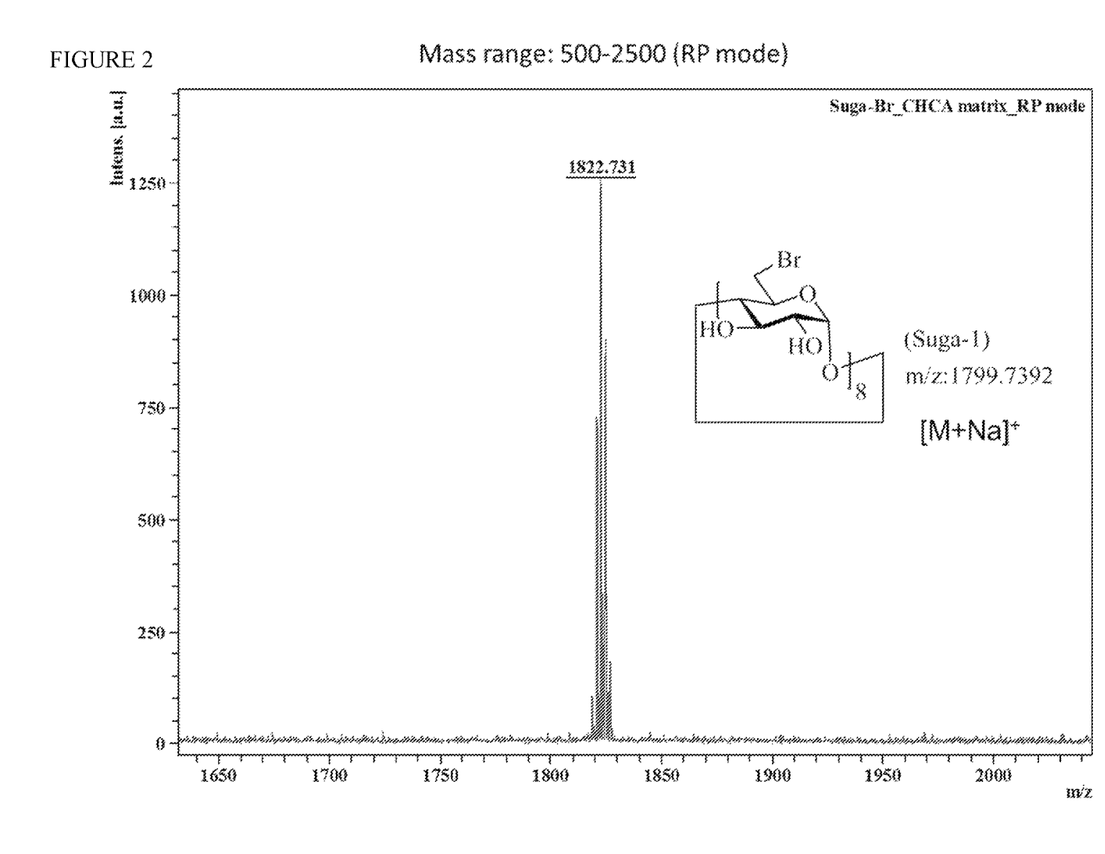
FIG. 2 is mass spectrum of Suga-1.
Figure 3:
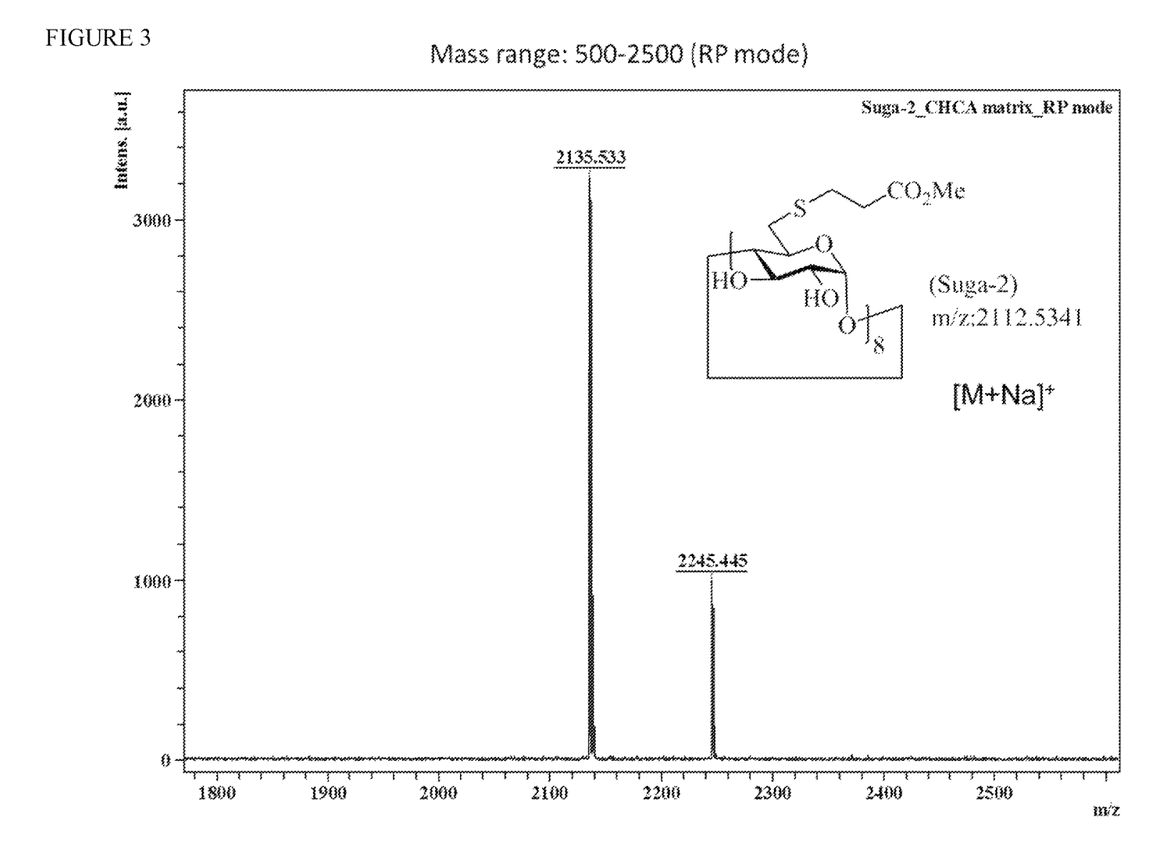
FIG. 3 is mass spectrum of Suga-2.
Figure 4:
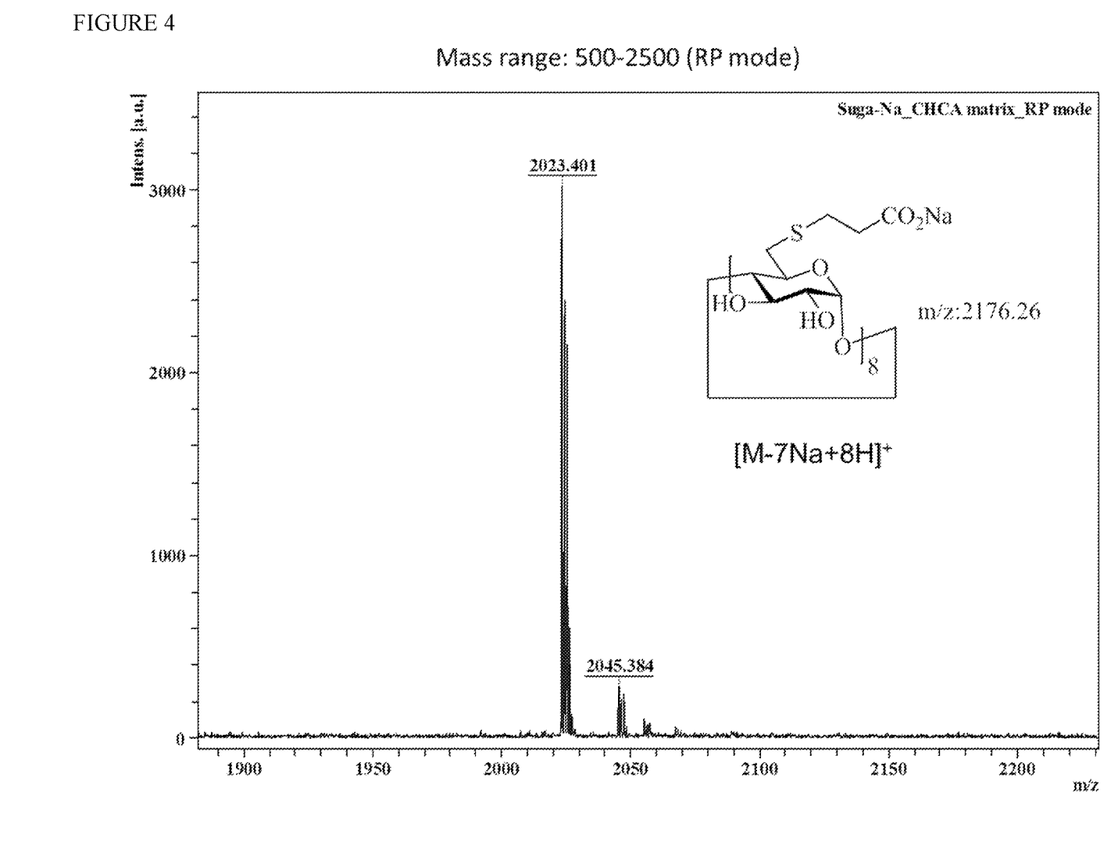
FIG. 4 is mass spectrum of Sugammadex sodium.
Figure 5:
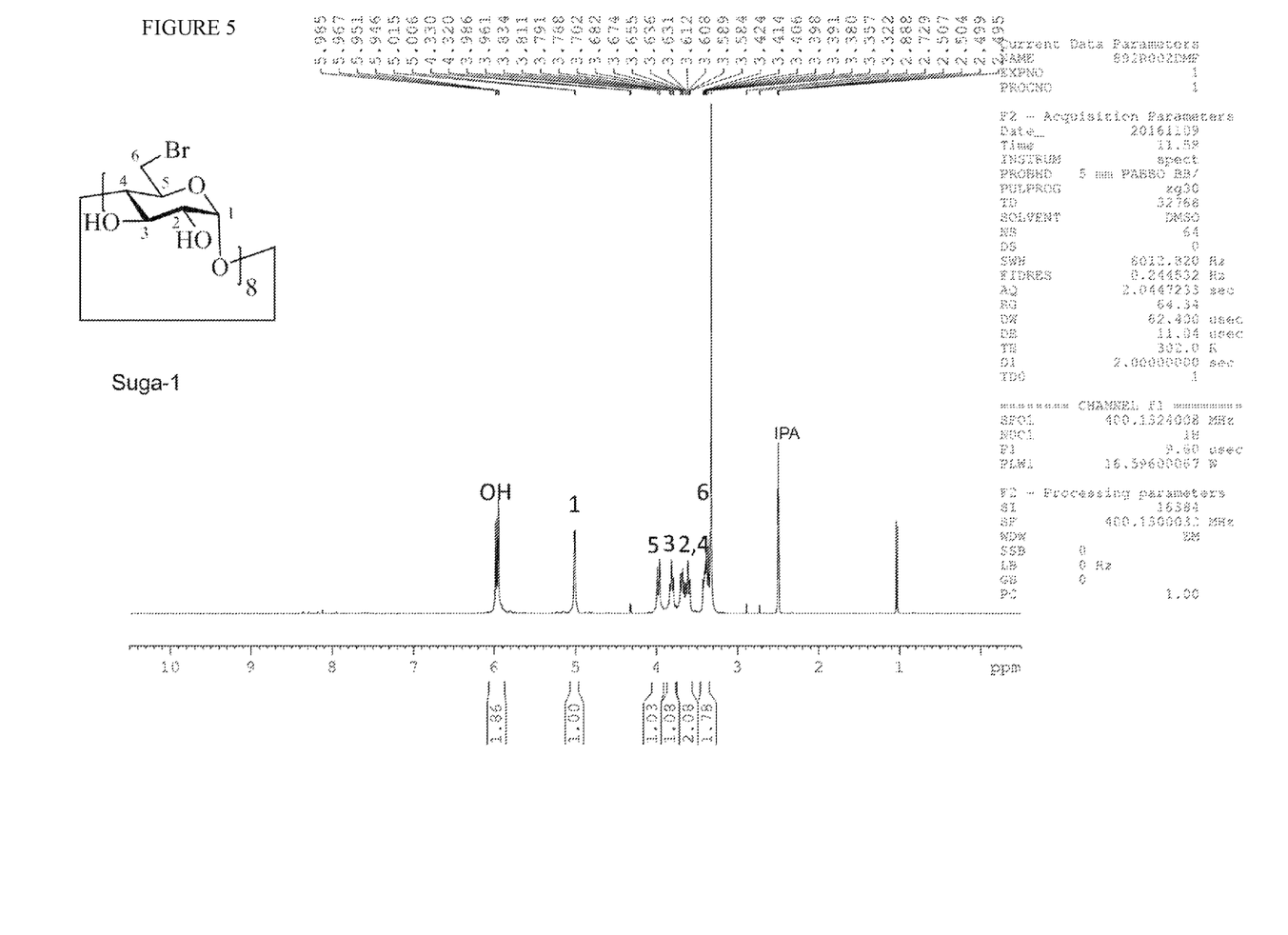
FIG. 5 is a $^1$H-NMR spectrum of Suga-1.
Figure 6:
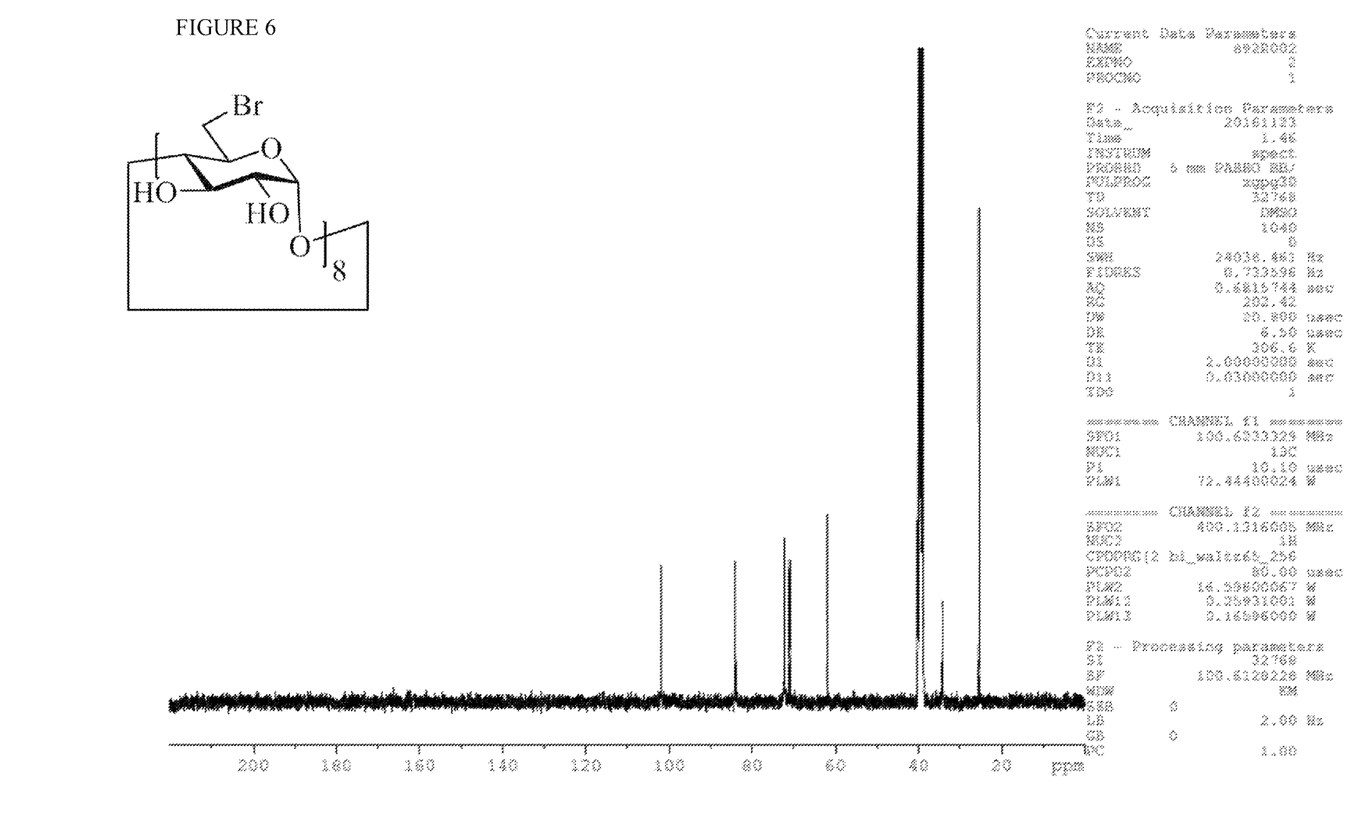
FIG. 6 is a $^{13}$C-NMR spectrum of Suga-1.
Figure 7:
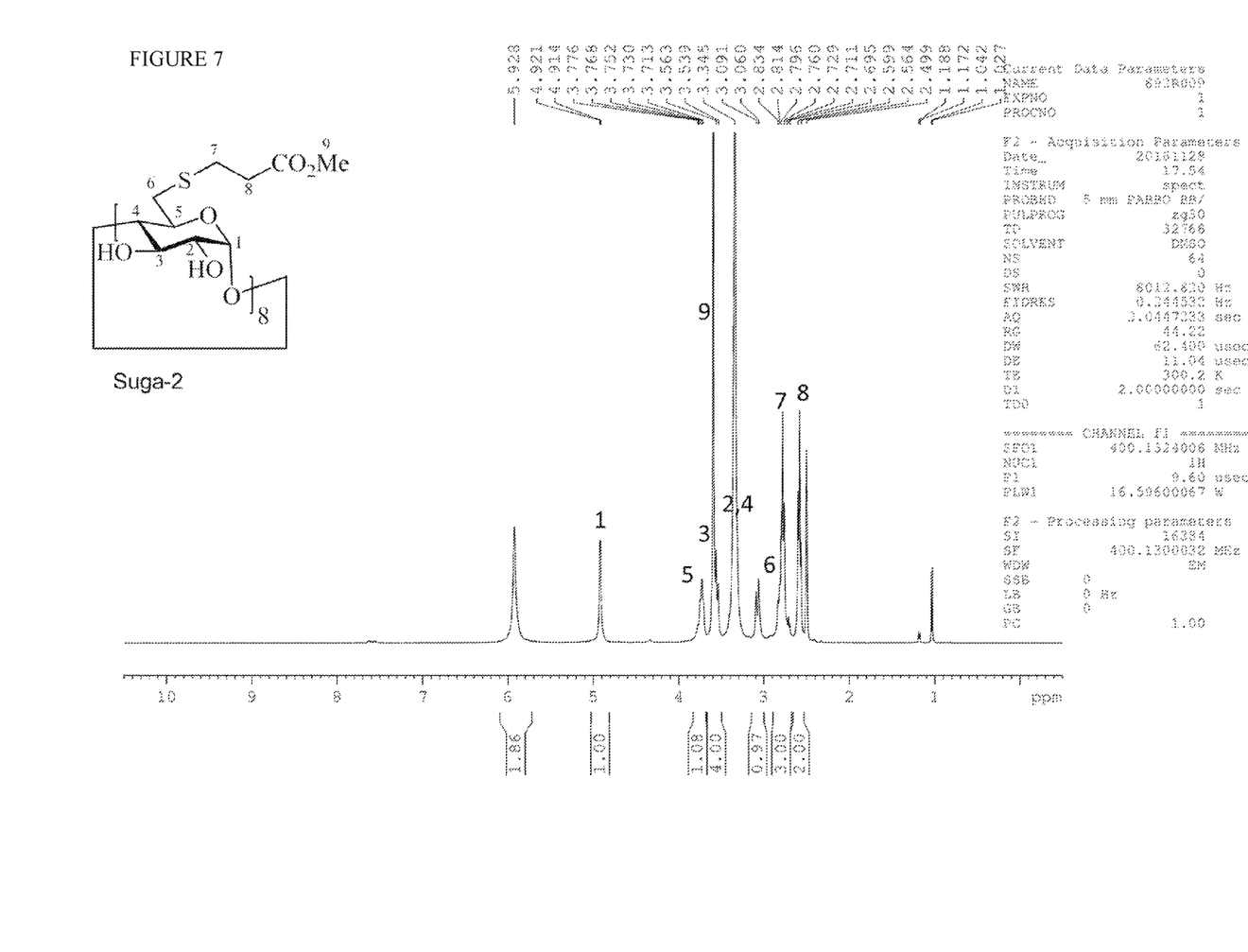
FIG. 7 is a $^1$H-NMR spectrum of Suga-2.
Figure 8:
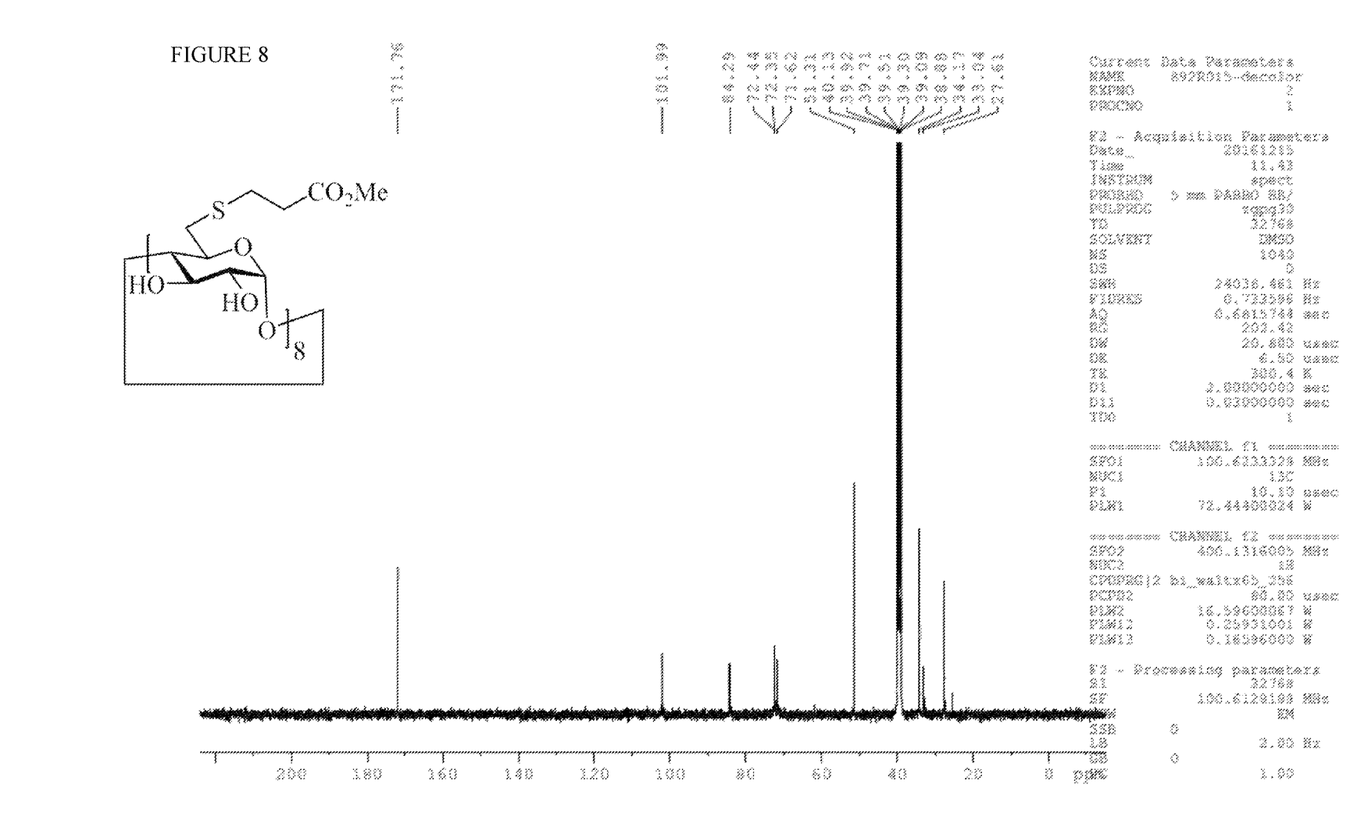
FIG. 8 is a $^{13}$C-NMR spectrum of Suga-2.
Figure 9:
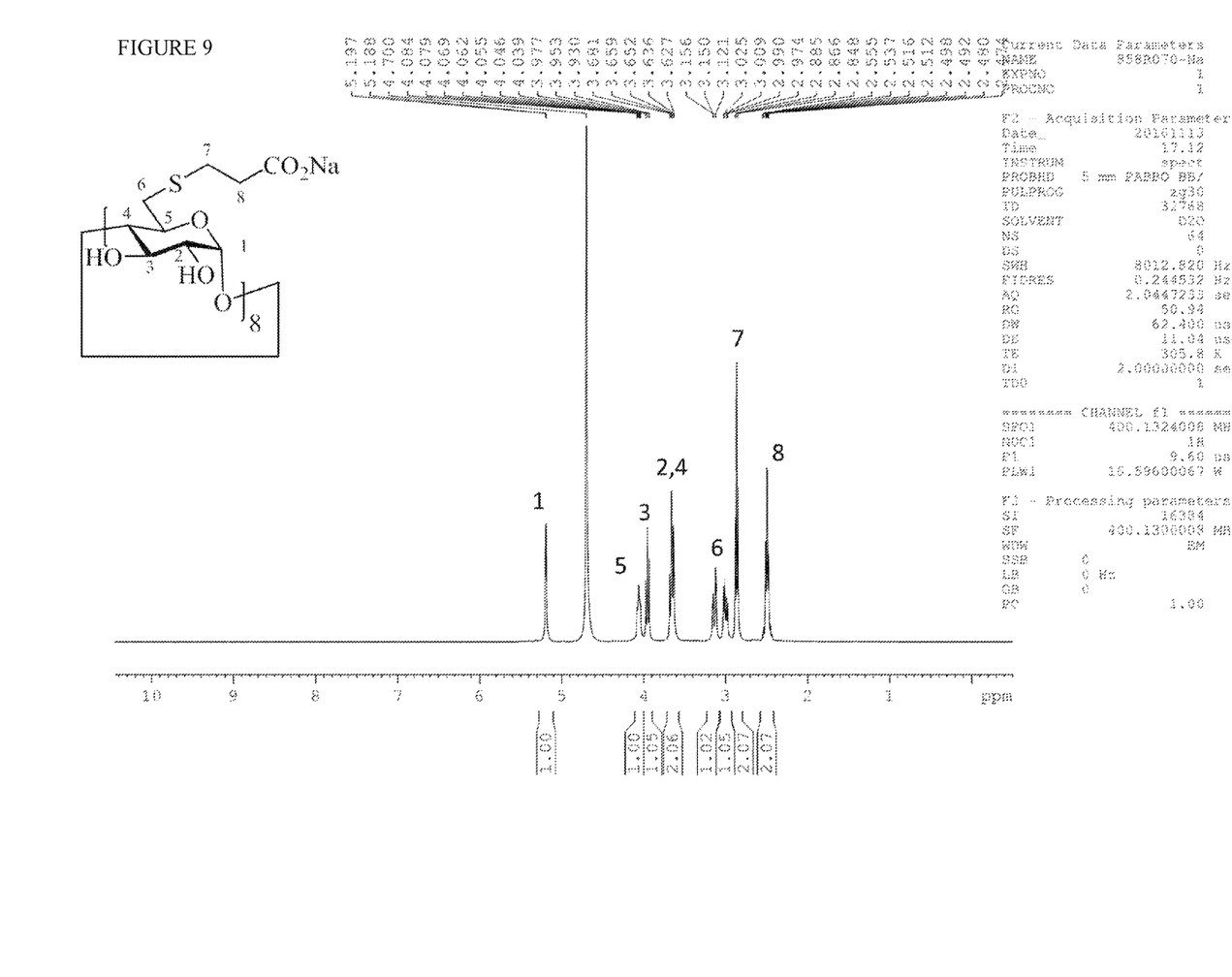
FIG. 9 is a $^1$H-NMR spectrum of Sugammadex sodium.
Figure 10:
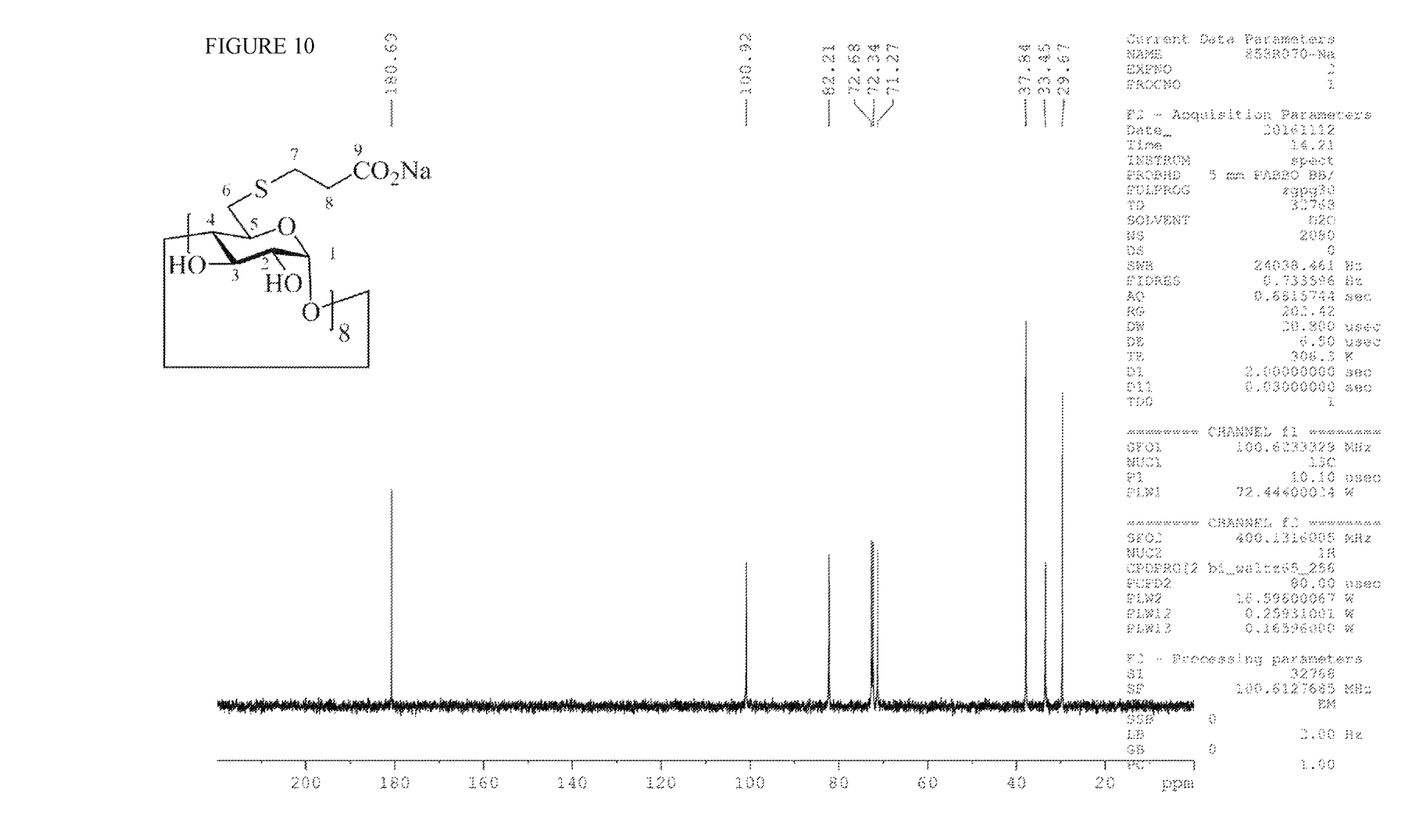
FIG. 10 is a $^{13}$C-NMR spectrum of Sugammadex sodium.

As used herein, "a," "an," "the," "at least one," and "one or more" are used interchangeably.

The present invention provides a method for preparation of Sugammadex sodium, comprising: (a) reacting gamma-cyclodextrin with tri-n-butylphosphine and $X_2$ in an organic solvent to obtain a compound of Formula I, wherein X is F, Cl, Br, or I;

Formula I (b) reacting the compound of Formula I with methyl 3-mercaptopropionate in presence of alkali metal hydride in an organic solvent at a temperature lower than 50° C. to obtain a compound of Formula II, and Formula II (c) reacting the compound of Formula II with sodium hydroxide to the Sugammadex sodium.

In one embodiment, $X_2$ is bromine and X is Br. In another embodiment, the alkali metal hydride is sodium hydride. In a further embodiment, the organic solvent is dimethylformamide.

In one embodiment, the temperature in step (b) is lower than 0° C. In another embodiment, the temperature in step (b) is in a range from 0° C. to −10° C. In still another embodiment, the temperature in step (b) is in a range from 0° C. to −5° C. In a further embodiment, the temperature in step (b) is in a range from 0° C. to −60° C. In a still further embodiment, the temperature in step (b) is in a range from 0° C. to −80° C.

In one embodiment, the method further comprises washing the compound of Formula I in step (a) with an alcohol. In another embodiment, the alcohol is isopropanol. In further embodiment, the method further comprises purifying the compound of Formula I by recrystallization from a solution comprising dimethylformamide and isopropanol before step (b).

In one embodiment, the method further comprises purifying the compound of Formula II by recrystallization from a solution comprising acetonitrile and water before step (c).

In another embodiment, the method further comprises adding alcohol to the Sugammadex sodium. In a further embodiment, the alcohol is methanol.

In one embodiment, the method further comprises purifying the Sugammadex sodium by crystallization from a solution comprising methanol and water. The purity of is above 99.0. In another embodiment, the purity is 99.3%

In one embodiment, the method further comprises purifying the Sugammadex sodium by sepharose Q column. The purity of is 98.0.

In one embodiment, the method further comprises desalting the Sugammadex sodium by a group consisting of reverse osmosis (RO) membrane filtration, tangential flow filtration, Sephadex G-10 column, or Sephadex G-25 column.

In one embodiment, the method further comprises spray drying the Sugammadex sodium to obtain an amorphous powder of the Sugammadex sodium.

The process of prior art uses triphenyl phosphine in step (a) rather than tri-n-butylphosphine. The reaction produces a large amount of bulky byproduct triphenylphosphine oxide (TPPO) which is difficult to remove from the product. However, the method of the present invention uses tri-n-butylphosphine and the resulting byproduct is tributylphosphine oxide (TBPO). The melting point of TBPO is lower than TPPO. The solubility of TBPO in isopropanol is better than TPPO. Thus, the product of the method of the present invention is easy to wash and the time of the method of the present invention can be reduced.

The reaction of step (b) in prior art is proceed under a temperature over 50° C. in basic condition. The reactant, 3-mercaptopropionic acid or methyl 3-mercaptopropionate, are unstable in this high temperature condition and degraded to form acrylic acid, methyl acrylate, and Sodium hydrosulfide (NaHS). NaHS is reactive to the compound of Formula I. Thus, the purity of this reaction is reduced. However, the method of the present invention is proceed at a temperature lower than 50° C. Therefore, the method of the present invention can reduce the reactive byproduct and increase the purity of the product.

EXAMPLE

The examples below are non-limited and are merely representative of various aspects and features of the present invention.

Example 1: Preparation of 6-per-deoxy-6-per-bromo-γ-cyclodextrin (Suga-1)

To a reaction flask, DMF (1.7 kg), Tributylphosphine (Bu$_3$P) (540 g, 2.67 mol) were added and stirred about 5 min. Bromine (420 g, 2.63 mol) was added to the reaction flask, kept the temperature at 20° C. to 30° C. and stirred for 20 min, Gamma-cyclodextrin (180 g, 0.139 mol) was suspended in DMF (850 g), and added to the reaction flask. After the addition, reaction mixture was heated to about 70° C. and stirred for 4-6 hrs. 25% Sodium methoxide solution (580 g) and MeOH (480 g) was added to quench the reaction, concentrated to remove methanol, and then water (4.5 kg) was added to form the precipitate, The crude Suga-1 was washed with water (200 g).

To a reaction flask, isopropanol (IPA) (2.83 kg), crude Suga-1 were added. The reaction mixture was heated to 35°

C. to 50° C., stirred for 1 hr to remove tributylphosphine oxide (TBPO), then recrystallization from DMF (380 g)/IPA (2.83 kg) solvent. The title compound (170 g) was obtained after filtration and washed with IPA (500 g).

Example 2: Preparation of 6-per-(2-carboxyethyl)thio-γ-cyclodextrin, methyl ester (Suga-2)

To a reaction flask, DMF (400 g), 60% NaH (50 g) were added under $N_2$. After the addition, the reaction mixture was de-gased and purged with $N_2$ literally three times. Methyl 3-mercaptopropionate (210 g, 1.75 mol), DMF (400 g) were added to the reaction flask which were cooled to −10° C. to 0° C. during the period of addition. After the addition, the temperature of the reaction flask was risen to −5° C. to 0° C. Suga-1 (170 g, 0.97 mol) in DMF (810 g) solution was added to the reaction mixture and stirred for 1-1.5 hrs. The reaction was completed by check with HPLC. Water (2.88 kg), ammonium chloride (320 g) aqueous solution were added to quench the reaction. The precipitate was formed gradually. The mixture was filtered, and the crude Suga-2 was obtained after washed with water (400 g). The pure title compound (200 g) white powder was obtained by recrystallization from Acetonitrile (1.57 kg)/water (1 kg) solution.

Example 3: Preparation of 6-per-(2-carboxyethyl)thio-γ-cyclodextrin, Sodium Salt (Sugammadex Sodium)

To a reaction flask, IN NaOH (30 g), water (700 g) aqueous solution, Suga-2 were added under $N_2$. The reaction mixture was stirred for 16 to 17 hrs. The pH of clear reaction solution was adjusted to 9 to 10 with 32% hydrochloride (10 g), water (140 g) aqueous solution, then methanol (1.5 kg) was added to form white powder of crude Sugammadex sodium. Pure wet Sugammadex sodium was obtained by recrystallization from methanol (330 g)/water (140 g) solution.

Example 4: Purification and Isolation of Crystalline Form I of 6-per-(2-carboxyethyl)thio-γ-cyclodextrin, Sodium Salt (Suagmmadex Sodium)

To a solution of 6-per-(2-carboxyethyl)thio-γ-cyclodextrin, sodium salt (1 g) in water (3 ml) was added DMF (7.5 ml) resulting in crystallization. The suspension was stirred for 1 h at 25° C., filtered and the cake was washed two time with a mixture of water and DMF to obtain crystalline form I of 6-per-(2-carboxyethyl)thio-γ-cyclodextrin, sodium salt. HPLC purity: 98.2%.

Example 5: Purification and Isolation of Crystalline Form II of 6-per-(2-carboxyethyl)thio-γ-cyclodextrin, Sodium Salt (Suagmmadex Sodium)

To a solution of 6-per-(2-carboxyethyl)thio-γ-cyclodextrin, sodium salt (174 g) in water (3 ml) was added MeOH (480 ml) resulting in crystallization. The suspension mixture was heated to 65° C., the solution turned clear. The mixture was cooled slowly. The crystals formed after the temperature lowered to about 42 to 45° C. and stirred for 2 hrs. The suspension was stirred for 2 h at 25° C., filtered and the cake was washed two time with a mixture of water and MeOH to obtain crystalline form II of 6-per-(2-carboxyethyl)thio-γ-cyclodextrin, sodium salt (140 g, yield 80.6%). HPLC purity: 99.3%.

Example 6: Purification and Isolation of 6-per-(2-carboxyethyl)thio-γ-cyclodextrin, Sodium Salt (Suagmmadex Sodium) by Column Packed with Sepharose Q Anion Exchange Resin Crude Sugammadex sodium (50 g) was dissolved in water (500 ml), then loaded on column packed with sepharose Q (750 ml) strong anion exchange resin. Highly Purified Sugammadex sodium (HPLC NLT 98.0%) was obtained by using sodium chloride aqueous solution as eluent (gradient elution: 0.02M to 0.6M). All the fractions of purified Sugammadex sodium aqueous solution was performed the de-salt procedure by column packed with sephadex G-10 or G25 to obtain de-salted Sugammadex sodium aqueous solution. The solution was concentrated in vacuo to reduce volume (600 ml).

Example 7: Purification and Isolation of Suagmmadex Sodium by Column Packed with Sepharose Q Anion Exchange Resin Crude Sugammadex sodium (50 g) was dissolved in water (500 ml), then loaded on column packed with sepharose Q (750 ml) strong anion exchange resin. Highly Purified Sugammadex sodium (HPLC NLT 98.0%) was obtained by using sodium chloride aqueous solution as eluent (gradient elution: 0.02M to 0.6M). All the fractions of purified Sugammadex sodium aqueous solution was performed the de-salt procedure by using reverse osmosis (RO) filtration or Tangential flow filtration (TFF) equipment to de-salted Sugammadex sodium aqueous solution. The solution was concentrated in vacuo to reduce volume (600 ml).

Example 8: Isolation of Amorphous Form of 6-per-(2-carboxyethyl)thio-γ-cyclodextrin, Sodium Salt (Suagmmadex Sodium)

The purified Sugammadex sodium aqueous solution from example 6 or example 7 was filtered with 0.2 μm filter paper prior to be performed the drying procedure. The conditions for spray drying was as follows.
Feed rate: 20 ml/min
Inlet temperature: 150° C.
Outlet temperature: 80° C.
The amorphous form of Sugammadex sodium (27 g) was obtained by Spray-dryer.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. A method for preparation of Sugammadex sodium, comprising:
   (a) reacting gamma-cyclodextrin with tri-n-butylphosphine and $X_2$ in an organic solvent to obtain a compound of Formula I,
   wherein X is F, Cl, Br, or I;

Formula I (b) reacting the compound of Formula I with methyl 3-mercaptopropionate in presence of alkali metal hydride in an organic solvent at a temperature lower than 0° C. to obtain a compound of Formula II, and Formula II (c) reacting the compound of Formula II with sodium hydroxide to form the Sugammadex sodium.

2. The method of claim 1, wherein $X_2$-is-bromine and X is Br.

3. The method of claim 1, wherein the alkali metal hydride is sodium hydride.

4. The method of claim 1, wherein the organic solvents in step (a) and step (b) are dimethylformamide.

5. The method of claim 1, which further comprises washing the compound of Formula I in step (a) with an alcohol.

6. The method of claim 5, wherein the alcohol is isopropanol.

7. The method of claim 5, which further comprises purifying the compound of Formula I by recrystallization from a solution comprising dimethylformamide and isopropanol before step (b).

8. The method of claim 1, which further comprises purifying the compound of Formula II by recrystallization from a solution comprising acetonitrile and water before step (c).

9. The method of claim 1, which further comprises adding alcohol to the Sugammadex sodium.

10. The method of claim 9, which further comprises purifying the Sugammadex sodium by recrystallization from a solution comprising methanol and water.

11. The method of claim 1, which further comprises purifying the Sugammadex sodium by a column packed with anion exchange resin.

12. The method of claim 1, which further comprises desalting the Sugammadex sodium by a group consisting of reverse osmosis (RO) membrane filtration, tangential flow filtration, or column filtration.

13. The method of claim 1, which further comprises spray drying the Sugammadex sodium to obtain an amorphous powder of the Sugammadex sodium.

* * * * *